United States Patent [19]

Gendler

[11] Patent Number: 5,556,430
[45] Date of Patent: Sep. 17, 1996

[54] FLEXIBLE MEMBRANES PRODUCED FROM ORGANIC BONE MATRIX FOR SKELETAL REPAIR AND RECONSTRUCTION

[76] Inventor: El Gendler, 917 S. Shenandoah, Los Angeles, Calif. 90035

[21] Appl. No.: 468,963

[22] Filed: Jun. 6, 1995

Related U.S. Application Data

[62] Division of Ser. No. 150,845, Nov. 12, 1993, Pat. No. 5,464,439, which is a division of Ser. No. 4,093, Jan. 13, 1993, Pat. No. 5,306,304, which is a continuation of Ser. No. 606,449, Oct. 31, 1990, abandoned.

[51] Int. Cl.$^6$ ....................................................... A61F 2/28
[52] U.S. Cl. .................................................. 623/16; 623/66
[58] Field of Search ................................. 623/16, 18, 66, 623/11, 10, 22, 23; 606/77, 151

[56] References Cited

U.S. PATENT DOCUMENTS

| | | | |
|---|---|---|---|
| 4,932,973 | 6/1990 | Gendler | 623/16 |
| 5,053,049 | 10/1991 | Campbell | 623/16 |

*Primary Examiner*—Debra S. Brittingham
*Attorney, Agent, or Firm*—Leydig, Voit & Mayer, Ltd.

[57] ABSTRACT

A flexible, organic bone matrix which is adapted for use during the in vivo repair, replacement or reformation of preselected portions of a mammalian or animal skeletal system comprising a continuous sheet of completely or partially demineralized natural bone, wherein the thickness of said sheet is such that the sheet has sufficient flexibility to allow the sheet to be shaped to conform to the configuration of a skeletal region to be repaired and sufficient tensile strength to allow the sheet to be so shaped without damage to the sheet. The matrix is ultimately resorbed by the body thereby eliminating the need for supplemental surgery to remove the matrix, as is presently necessary when other exogenous, membrane materials are used. A method for the in vivo repair or replacement of a preselected section of a mammalian or animal skeletal system utilizing said matrix is also disclosed.

3 Claims, No Drawings

FLEXIBLE MEMBRANES PRODUCED FROM ORGANIC BONE MATRIX FOR SKELETAL REPAIR AND RECONSTRUCTION

This is a divisional application Ser. No. 08/150,845, filed on Nov. 12, 1993, now U.S. Pat. No. 5,464,439, which is a divisional of Ser. No. 08/004,093, filed Jan. 13, 1993, now U.S. Pat. No. 5,306,304, which is a continuation of Ser. No. 07/606,449, filed Oct. 31, 1990, abandoned.

FIELD OF THE INVENTION

The present invention relates to implants for use in the repair and replacement of the various portions of the human skeletal system. More particularly, it is directed toward implants for use in clinical procedures such as sinus elevation, nasal-oral fistula, mandibular augmentation, poncho cover for the salvage of peri-implantitis, guided tissue regeneration, and related procedures.

BACKGROUND OF THE INVENTION

The repair, as well as the replacement, of diseased and damaged human bone have been the subject of substantial research efforts over the past several decades. This research has yielded advances in the reconstruction of many areas of the human skeletal system. As a result of these advances, replacements and repair are presently being undertaken in several areas including the restructuring of the craniofacial system, the introduction of artificial knee and hip joints, and the application of additional features during cosmetic surgery.

The biological mechanisms underlying the aforesaid reconstruction and repair varies according to the type of bone implant selected. New bone can be formed by three basic mechanisms: osteogenesis, osteoconduction and osteoinduction. In osteogenic transplantation, viable osteoblasts and peri-osteoblasts are moved from one body location to another where they establish centers of bone formation. Cancellous bone and marrow grafts provide such viable cells.

In the transplantation of large segments of cortical bone or allogenic banked bone, direct osteogenesis does not occur. In these cases, osteoconduction transpires—the dead bone acts as a scaffold for the ingrowth of blood vessels, followed by the resorption of the implant and deposition of new bone. This process is very slow however, often requiring years to reunite a large segmental defect.

Osteoinduction is the phenotypic conversion of connective tissue into bone by an appropriate stimulus. As this concept implies, formation of bone can be induced at even non-skeletal sites. Osteoinduction is the preferred method of providing new bone growth as grafts of this type are typically incorporated into the host bone within a two week period. In contrast, osteoconductive grafts have been found to be non-incorporated as long as one year after implantation.

In order to provide an environment suitable for osteoinduction, a material should be selected which is not only capable of inducing osteogenesis throughout its volume, but is also biocompatible, non-inflammatory, and possesses the ability to be ultimately resorbed by the body and replaced with new, natural bone.

One approach to bone repair and reconstruction is disclosed in U.S. Pat. Nos. 4,472,840 and 4,394,370. These references, the second being a divisional of the first, are directed toward bone graft material and a method of inducing bone growth which center upon a material which comprises a complex of reconstituted collagen and demineralized bone particles. This material may be fabricated into many forms, such as thin membranes, gels, or preferably a sponge-like configuration, depending upon the particular application. One purported advantage of this material, as stated in the reference, is in its ability to promote bone regeneration. For example, the use of bone particles in implant materials has been shown to induce greater quantities of new bone growth than unmodified, larger particles such as blocks or chips. Moreover, large, unmodified sections of demineralized bone appear to induce osteogenesis only at their surface, not within the graft itself.

A similar approach is found in U.S. Pat. Nos. 4,485,096 and 4,485,097 which disclose the use of bone particulates, or powders. Bone-equivalents are prepared by incorporating bone powder into hydrated collagen lattices contracted with fibroblast cells prepared in accordance with this reference. This allows the material to be cast into any shape desired, such as sheets. Certain methods and devices have been developed to assist in the casting of this material into sheets. One method requires the material to be coated onto a mesh of polytetrafluoroethylene (PTFE) or stainless steel which serves to maintain the length and width of the material. The inclusion of such a dimensional stabilizing material is required due to the presence of fibroblast cells. If left unrestrained, the collagen lattice would undergo contractions in all dimensions.

A related type of material which may be used as a bone substitute is found in U.S. Pat. No. 4,430,760. This reference discloses a bone prosthesis comprising demineralized bone or dentin powder contained in a porous medical grade casing. This casing is manufactured from biocompatible polymeric fibers or a microporous membrane. Crosslinked collagen is the preferred material. This material may be used to replace or repair non-stress bearing bone tissue, i.e., craniofacial bone other than load-bearing parts of the jaw. Demineralized bone powder is advantageously used because, as a particulate, it is more readily and completely invaded by osteogenic cells than solid, one-piece demineralized bone.

Yet another material is described in U.S. Pat. No. 4,678,470 which provides a bone grafting material which is produced from allogenic or xenogenic bone which may be pulverized, used as a large block, or machined into a precise pre-determined shape depending on the bone defect being repaired. The method for deriving the material comprises tanning the bone with glutaraldehyde. This treatment of the material serves to stabilize the material as well as cross-link the proteins. The bone may also be demineralized, if desired. The resulting demineralized bone will have a "spongier" texture and thus finds use only in non-weight bearing situations, i.e., repair of small defects, filling of small tunnels or other hollow areas, cosmetic surgery, and similar uses.

Present processes used in the field of periodontics also utilize an expanded polytetrafluoroethylene material, e.g., GORE-TEX® e-PTFE, which is stated to be flexible and biocompatible. One example of an application of such material is when it is implanted next to a tooth root after extraction of a tooth. Such implantation with this material allegedly isolates the root from the epithelium and connective tissue such that only alveolar bone and connective tissue fill the space. This material superficially attaches itself to the body, a second surgical procedure being required to remove the material from the patient after sufficient bone growth has occurred.

Thus, and despite the materials known in the art, there exists a need for a material that possesses all of the aforementioned advantageous properties, e.g., biocompatible, non-inflammatory, capable of inducing osteogenesis, the ability to be ultimately resorbed by the body and replaced with natural bone, while not sacrificing flexibility for strength or dimensional stability and, importantly, not requiring a second surgical procedure to remove the implant or a portion thereof.

SUMMARY OF THE INVENTION

It has now been surprisingly discovered that completely or partially demineralized organic bone matrix can be sliced into thin sheets or membranes and that such sheets have totally unexpected properties. The sheets are flexible while exhibiting significant tensile strength. Thus, the present invention provides a membrane produced from demineralized organic bone matrix which is useful for the in vivo repair, replacement or reformation of preselected portions of a skeletal system. The membrane comprises a continuous sheet of demineralized natural bone, having a thickness such that the sheet has sufficient flexibility to allow the sheet to be shaped to conform to the configuration of a skeletal region to be repaired and sufficient tensile strength to allow the sheet to be so shaped without damage to the sheet.

Furthermore, there is provided a method for the in vivo repair or replacement of a preselected section of an animal or mammalian skeletal system comprising affixing to said section a continuous flexible sheet of demineralized natural bone to the section, wherein the thickness of said sheet is such that the sheet has sufficient flexibility to allow the sheet to be shaped to conform to the configuration of a skeletal region to be repaired and sufficient tensile strength to allow the sheet to be so shaped without damage to the sheet.

An additional method is drawn toward the in vivo reformation of an animal or mammal which comprises inserting a continuous sheet of demineralized natural bone into said animal or mammal, wherein the thickness of said sheet allows for the induction of osteogenesis throughout the volume of the sheet.

DETAILED DESCRIPTION OF THE INVENTION

While the present invention will be described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The present invention provides a novel material and method for the repair and replacement of a portion of a skeletal system, e.g., the human skeletal system. The material comprises a continuous sheet of demineralized natural bone having a predetermined and therapeutically advantageous thickness. This material is biocompatible, non-inflammatory, capable of inducing osteogenesis, and has the ability to be ultimately readsorbed by the body and replaced with natural bone. Further, the aforementioned material surprisingly is flexible while retaining its structural and dimensional integrity both prior to and after hydration and additionally possessing significant tensile strength.

Although demineralized bone heretofore has existed in the art, no one has previously produced demineralized bone in the form of thin sheets or membranes. Indeed, it is quite surprising and unexpected that a thin sheet of completely or partially demineralized bone could be produced having both significant flexibility and tensile strength. Nothing in the art heretofore indicated that such a thin sheet of demineralized bone could be made, let alone that it could exhibit such desirable flexibility and tensile strength.

The bone itself may be produced from any natural bone. Generally, the bone material is harvested from any suitable vertebrate. The harvested material may be further processed by various techniques to remove substantially all blood and lipid residue. The resulting bone may be cut into plates of approximately 0.5–1.5 mm in thickness using, e.g., an Isomet Plus precision saw (Buehler LTD., Lake Bluff, Ill.) which has a diamond wafering blade mounted thereon. Cutting of the bone should be undertaken with continuous irrigation of the blade to prevent unwanted heating of the bone. The resulting plates may be further processed to remove any remaining blood and lipids.

Demineralization of the bone is subsequently conducted by any known method, e.g., subjecting the bone to different acids, chelating agents, electrolysis or any combination of the foregoing. If desired, the bone may be perforated according to U.S. Pat. No. 4,932,973, the specification of which is herein incorporated by reference, prior to demineralization, this serving to increase the osteoinductivity of the final bone product.

It has been discovered that the aforementioned demineralized bone matrix, when machined to a certain thickness, induces osteogenesis throughout its thickness and ultimately is substantially completely resorbed by the living system into which it is implanted. Further, the matrix is flexible. Generally, the thickness at which this will occur ranges up to about 10 millimeters. Advantageously, the thickness will range from about 0.05 to about 1.5 millimeters, and the thickness preferably ranges from about 0.7 to about 1.2 millimeters.

In accordance with the aforesaid dimensions, natural bone sheets having a length and width of up to about 25 by 500 millimeters may be produced, this being limited only by the dimensions of the bone material supplied. The material may then be reduced to the desired length and width dimensions by cutting. Use of the term "sheet" throughout this disclosure is intended to encompass those portions of an original sheet which have been reduced to a desired length and width.

The present material is further capable of osteoinduction despite the absence of any attachment to existing bone or cartilage. This use of the material in this manner is generally made during the reconstruction of areas which have incurred massive bone loss.

The following examples, which are not intended as limiting the scope of the invention, illustrate the osteogenesis capabilities of the present material.

EXAMPLE 1

Maxillary Sinus (Sub-atral) Augmentation Elevation

Bone thickness in the floor of this sinus is often inadequate for dental implants. The problem is typically approached by opening a bone window and lifting a plate of bone to push the mucous membrane of the sinus away from the bone, creating a new space to contain bone graft for more secure implantation. Rarely, this membrane may be torn, predisposing the area to infection. The bone of the present invention may be used as a patch in this situation, thus avoiding delayed and necessary subsequent surgical procedures.

EXAMPLE 2

Oro-nasal Fistula

The oral and nasal cavities are compartmentalized by bone plates which may become deficient, this creating abnormal passages in these cavities which interfere with swallowing, secretions, and speech. Restoration of the function requires restoration of form, i.e., the insertion of a bone plate. This may be difficult using known methods but may be accomplished easier and more successfully using the material of the present invention which may be machined to a similar thickness and which will induce new bone growth.

EXAMPLE 3

Alveolar Augmentation

Aging and disuse atrophy cause bone loss from the tooth socket portion of the jaws. These parts cannot be loaded, for example with a dental prosthesis, unless metal implants are inserted. However, these metal implants can only be properly implanted where there exists an adequate bone surface. Various methods have been attempted to build up this alveolar area with limited success. For example, powders tend to migrate from their original placement, particularly when this placement is in a mandibular or maxillar location or on the crest of such a ridge. The present invention may be employed by, for example, successively layering of the material over the atrophied bone. Alternatively, it may be used to cover and contain particulates which have been inserted to increase bone mass.

EXAMPLE 4

"Poncho" For Guided Tissue Regeneration In Periodontal Disease

Bone is frequently resorbed from around teeth (periodontal disease) or around a metal implant. These structures cannot function without firm bone support and will be ultimately lost. Particulate materials are typically placed in the semi-circular defect and are covered with a sheet of e-PTFE which allegedly prevents invasion of certain unwanted tissue forming cells. Use of the present material functions as such a limiting membrane but is not a foreign body, is not predisposed to infection and does not require a subsequent second surgical procedure to remove same.

Additional examples of uses for the present material include the replacement, augmentation and recontouring of natural bone structures in plastic and reconstructive surgery, cosmetic, otolaryngolical, and neurological surgical procedures.

In view of the material's ability to be reabsorbed into the living system after promoting osteogenesis, a subsequent surgical procedure to remove any remaining portion of the material is totally eliminated.

Other advantages include the flexibility of the material. The material is flexible at the time it is manufactured as well as after hydration. By use of the term "flexible," it is contemplated that the material may be deformed or bent from its original configuration. Flexibility is a desirable property because it is often desirable to be able to bend and shape the material such that, after the area is completely healed, the contour of the bone being repaired matches the contour of the original bone, or matches the original bone as closely as possible. Also, specific surgical procedures benefit from this characteristic, such as those described in the previous Examples.

The material also advantageously provides a tensile strength which is higher than other materials which are capable of osteoinductive activity throughout the volume of the material.

Generally, the method for using the present natural bone sheet comprises affixing the material onto the portion of the skeletal system in need of repair or replacement. Affixation may be accomplished by any known surgical technique.

In addition, the present sheet can be implanted without being affixed to existing bone, for example, during submucosal tunnelling and demineralized bone sheet insertion for maxillary/mandibular ridge augmentation.

Although the present material and methods are useful in humans, they will also be found useful in treating many different types of animals, e.g., horses, dogs and the like.

What I claim is:

1. A method for the production of a flexible organic bone sheet having a predetermined thickness useful for the in vivo repair or replacement of preselected portions of an animal skeletal system comprising machining natural bone to form said continuous sheet having a thickness up into about 1.5 millimeters, and subsequently demineralizing said sheet, wherein the thickness of said sheet is such that the sheet has sufficient flexibility to allow the sheet to be shaped to conform to the configuration of a skeletal region to be repaired and sufficient tensile strength to allow the sheet to be so shaped without damage to the sheet.

2. The method of claim 1, wherein the thickness of said sheet ranges from about 0.05 to about 1.5 millimeters.

3. The method of claim 1, wherein the thickness of said sheet ranges from about 0.7 to about 1.2 millimeters.

* * * * *